United States Patent [19]

Sitzmann et al.

[11] Patent Number: 4,546,200

[45] Date of Patent: Oct. 8, 1985

[54] 2,2-DINITROBUTANE-1,4-DIOL AND MONOESTERS

[75] Inventors: Michael E. Sitzmann, Adelphi; Horst G. Adolph, Silver Spring, both of Md.

[73] Assignee: The United States of America as represented by the Secretary of the Navy, Washington, D.C.

[21] Appl. No.: 492,277

[22] Filed: May 6, 1983

[51] Int. Cl.[4] ............................................. C07C 69/52
[52] U.S. Cl. ...................................... 560/222; 560/8; 560/103; 560/105; 560/205; 560/226; 560/227; 560/230; 560/231; 560/253; 568/712
[58] Field of Search ................ 568/712; 560/264, 222, 560/8, 105, 205, 226, 227, 230, 231, 253

[56] References Cited

U.S. PATENT DOCUMENTS

| | | | |
|---|---|---|---|
| 3,000,933 | 9/1961 | Herzog | 560/264 |
| 3,396,187 | 8/1968 | Benziger et al. | 560/264 |
| 3,590,067 | 6/1971 | Gold et al. | 560/264 |

FOREIGN PATENT DOCUMENTS 650551 10/1962 Canada ............................... 568/704

*Primary Examiner*—Paul J. Killos
*Attorney, Agent, or Firm*—Robert F. Beers; Kenneth E. Walden; Roger D. Johnson

[57] ABSTRACT

2,2-Dinitrobutane-1,4-diol and 4-monoesters thereof.

11 Claims, No Drawings

2,2-DINITROBUTANE-1,4-DIOL AND MONOESTERS

BACKGROUND OF THE INVENTION

This invention relates to alcohols and more particularly to energetic polynitro substituted diols.

Polynitro-hydroxy terminated diols are being used to prepare energetic binders for propellants and explosives. Lower molecular weight polynitro alcohols have been used as building blocks to prepare these diols. Because of the limitation on the choice of these building blocks, the high energy diols have been limited to those having gem-dinitro groups in the $\beta$ position to the hydroxy groups,

Unfortunately while these diols have excellent energy content, they are unstable in the presence of weak bases or nucleophiles (such as atmospheric moisture) or oxygen and nitrogen containing components of the energetic binder systems. They deformylate producing formaldehyde and labile dinitromethane derivates which contaminate and cause the degradation of the binder systems.

U.S. patent application Ser. No. 6-453,675 entitled "3,3,3-trinitropropanol" and a method of preparation thereof, filed on Dec. 27, 1982 by Horst G. Adolph, discloses a nitro alcohol of the formula $C(NO_2)_3CH_2CH_2OH$ which does not deformylate under basic conditions as do 2,2,2-trinitroethanol, $C(NO_2)_3CH_2OH$, and 2,2-dinitropropanol, $CH_3(NO_2)_2CH_2OH$. However, because it is a mono alcohol, 3,3,3-trinitropropanol can not be used to form energetic binder polymers.

It would be desirable, therefore, to produce energetic polynitro diols which would be stable under weak basic conditions. Moreover, this should be done with a minimum reduction in the energy content of the binder system. However, before this can be done, new intermediates must be provided for the preparation of the diols.

SUMMARY OF THE INVENTION

Accordingly, an object of this invention is to provide new organic compounds.

Another object of this invention is to provide new energetic polynitro organic compounds.

A further object of this invention is to provide new polynitro organic compounds which can be used to synthesis new stable, energetic polynitrodiols.

These and other objects of this invention are accomplished by providing 2,2-dinitrobutane-1,4-diol and 4-monoesters thereof.

DETAILED DESCRIPTION OF THE PREFERRED EMBODIMENT

The title diol, $HOCH_2C(NO_2)_2CH_2CH_2OH$, has a gem-dinitro group $\beta$ to a hydroxy group. Thus, it will undergo deformylation in the presence of weak bases. Nevertheless, this diol is useful as a building block for the preparation of energetic diols which will not deformylate in the presence of weak bases.

U.S. Navy Case No. 66,880, entitled "5-Aza-3,3,7,7-tetranitrononane-1,9-diols and methods of Preparation," by Horst G. Adolph and Michael E. Sitzmann, filed concurrently with the present application and herein incorporated by reference, discloses the preparation of energetic diols from 2,2-dinitrobutane-1,4-diol and 2,2-dinitrobutane-1,4-diol-4-acetate. For instance, 2,2-dinitrobutane-1,4-diol was reacted with ammonia to produce 5-aza-3,3,7,7-tetranitrononane-1,9-diol,

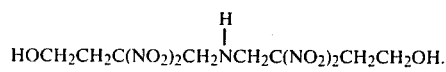

The active hydrogen on the nitrogen atom can be replaced by more energetic group such as —NO or —NO$_2$.

Preparation of the starting material 3,3,3-trinitropropanol is illustrated by example 1.

Example 2 illustrates the preparation of 2,2-dinitrobutane-1,4-diol. First 3,3,3-trinitropropanol is reacted with potassium iodide to produce the salt potassium 3,3-dinitropropanol.

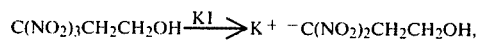

The salt is reacted with formaldehyde and the solution is acidified to yield 2,2-dinitrobutane-1,4-diol.

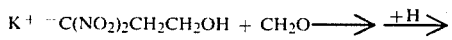

Monoesters of 2,2-dinitrobutane-1,4-diol in which the 4-hydroxy position is blocked may be formed by the following procedure. First, 3,3,3-trinitropropanol is esterfied. This can be done by any conventional method such as reacting the alcohol with the appropriate acid chloride

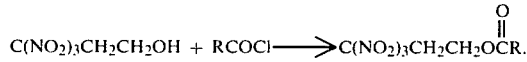

The remaining steps are the same as those used in preparing the diol. The 3,3,3-trinitropropanol ester is reacted with potassium iodide to form the salt

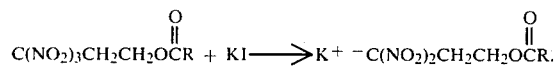

Reaction of the salt with formaldehyde followed by acidification of the reaction solution yields the corresponding 4-monoester of 2,2-dinitrobutane-1,4-diol,

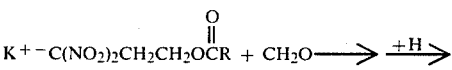

Because the

serves only as a blocking group and is later hydrolyzed off, selection of R is not critical. For example, R may be an alkyl, fluoroakyl, chloroalkyl, aryl, fluoroaryl, chloroaryl, aralkyl, fluoroaralkyl, chloroaralkyl, or alkene group. The only restrictions are that R should contain no groups that will interfere with the esterification of the 3,3,3-trinitropropanol or with the reaction between the 2,2-dinitrobutane-1,4-diol monoester and ammonia. (Amino and hydroxy containing groups are therefore not included in R.) As a practical matter, R is preferably low in molecular weight. For example, when R is an alkyl, fluoroalkyl, or chloroalkyl group, R preferably contains from 1 to 12, and more preferably from 1 to 4 carbon atoms. When R is an aryl, fluoroaryl, or chloroaryl groups, R preferably contains from 6 to 18, and more preferably 6 carbon atoms. When R is an aralkyl, fluoroaralkyl, or chloroaralkyl group, R preferably contains from 7 to 18, and more preferably from 7 to 10 carbon atoms. Of all the groups available, R equals to —CH$_3$ is most preferred for industrial purposes because of cost. Other common examples are R equal to

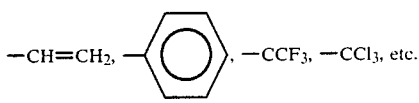

The monoester can be reacted with ammonia to form a diester

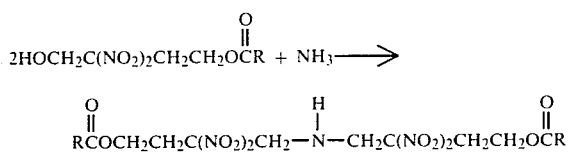

which is then hydrolyzed to produce 5-aza-3,3,7,7-tetranitrononane-1,9-diol

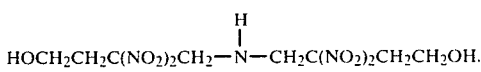

Conditions for the reaction with ammonia and the subsequent hydrolysis of the ester groups is disclosed in U.S. Navy Case No. 66,880 entitled "5-Aza-3,3,7,7-tetranitrononane-1,9-diols and Methods of Preparation," by Horst G. Adolph and Michael E. Sitzmann, filed concurrently with the present application and herein incorporated by reference.

Examples 3, 4 and 5 of this specification disclose the preparation of 2,2-dinitrobutane-1,4-diol-4-acetate (i.e., R=CH$_3$).

The general nature of the invention having been set forth, the following examples are presented as specific examples thereof. It will be understood that the invention is not limited to these specific examples but is susceptible to various modifications that will be recognized by one of ordinary skill in the art.

EXAMPLE 1 (PRIOR ART)

Preparation of 3,3,3-trinitropropanol 4,4,4-Trinitrobutyric acid (210 g, 0.94 mol) was added to 534 ml (908 g) of trifluoromethanesulfonic acid stirred in a 2000 ml, 3-neck, round-bottom flask. The solution was heated to 60° C. (oil bath) and sodium azide (100 g, 1.54 mol) was added in approximately 2 g portions over a six-hour period. (A stream of nitrogen was kept flowing over the reaction mixture during the addition to dilute and expel excess HN$_3$.) Stirring was stopped and the thick mixture was heated overnight at 50° C. before it was poured onto ice to give an aqueous solution (2500 ml) which was extracted with 3×300 ml of methylene chloride. Two grams of unreacted trinitrobutyric acid were recovered from the CH$_2$Cl$_2$ extracts. The aqueous solution was cooled at 10°–14° C. while a solution of 140 g of sodium hydroxide in 200 ml of water was added dropwise with good stirring. The solution was then heated to 35° C. before a solution of 121 g (1.75 mol) of sodium nitrite in 400 ml of water was added over a 30 minute period. (Some cooling was necessary to maintain the temperature at approximately 40° C. during the addition.) The solution was heated at 60° C. for one and a half hours before it was cooled to 25° C. and extracted with 2×500 ml methylene chloride. It was then saturated with sodium chloride and extracted with 3×500 ml CH$_2$Cl$_2$. The combined extracts contained 161 g (87.7 percent) of crude 3,3,3-trinitropropanol.

EXAMPLE 2

Preparation of 2,2-Dinitrobutane-1,4-diol

A mixture of 13.5 g of 3,3,3-trinitropropanol and 23.0 g of potassium iodide in 200 ml of methanol was stirred at 35°–40° C. for 2–3 days, allowed to cool to room temperature, and the precipitated potassium 3,3-dinitropropanol was isolated by filtration and washed with cold methanol. The methanol wet salt was added with ice cooling and stirring to a mixture of 100 ml of water and 6.0 g of 37% formalin. With continued stirring and cooling, the mixture was slowly (3 minutes) acidified with concentrated HCl to a pH of about 2.5–3 and stirred another 2 hours. After further acidification with concentrated HCl and saturation with NaCl, the solution was extracted 5 times with ether, the extracts were dried (MgSO$_4$), filtered, and freed from solvent in vacuo to give 9.0 g of solid (mp 47°–55° C.) which was stirred with 80 ml of chloroform at ambient temperature to give 7.85 g of white solid, mp 55°–57° C. Crystallization from methylene chloride gave 7.2 g, mp 56°–58° C., $^1$H-NMR (CD$_2$Cl$_2$): δ4.65 (d, 2H), 3.95 (m, 2H), 3.35 (t, 1H), 2.92 (t, 2H), 2.12 (t, 1H).

Analysis
Calculated for C$_4$H$_8$N$_2$O$_6$: C, 26.67; H, 4.48; N, 15.55.
Found: C, 26.62; H, 4.51; N, 15.42.

EXAMPLE 3

Preparation of 3,3,3-Trinitropropyl Acetate

Acetyl chloride (125 ml) was added to a dried (MgSO$_4$) solution of 150 g of crude 3,3,3-trinitropropanol in 2000 ml of methylene chloride cooled in an ice bath. The solution was slowly warmed to reflux temperature and held overnight. The reaction solution was concentrated to 800 ml by distillation before it was cooled and poured onto ice water. The mixture was stirred for 30 minutes before the CH$_2$Cl$_2$ layer was separated, dried over MgSO$_4$ and the solvent removed to give 183 (100%) of crude trinitropropyl acetate as a light green solid.

A similar reaction employing 31.0 g of crude 3,3,3-trinitropropanol, 50 ml of methylene chloride and 25 ml of acetyl chloride gave, after addition of hexane to the CH$_2$Cl$_2$ solution and chilling, filtering off the solid, concentrating and chilling again, 34.5 g (88.9%) of 3,3,3-trinitropropyl acetate. A second recrystallization from CH$_2$Cl$_2$/hexane gave material of mp 47°–49° C.;

$^1$H-NMR (CDCl$_3$):δ2.06 (s, 3H), 3.45 (t, 2H), 4.55 (t, 2H).

Analysis:

Calculated for C$_5$H$_7$N$_3$O$_8$: C, 25.32; H, 2.98; N, 17.72. Found: C, 25.31; H, 3.01; N, 17.27.

EXAMPLE 4

Preparation of Potassium 3,3-dinitropropyl acetate

Potassium iodide (338 g, 2.03 mol) was added to 183 g (0.77 mol) of crude 3,3,3-trinitropropyl acetate in 2100 ml of methanol. The mixture was stirred at 40° C. for 24 hours before it was cooled to 20° C. and the yellow salt removed by filtration. The product was stirred with 600 ml of methanol at 20° C. to give 88.5 g (50%) of yellow salt.

A similar reaction using 32.1 g of purified 3,3,3-trinitropropyl acetate gave 20.4 g (66%) of potassium 3,3-dinitropropyl acetate. $^1$H-NMR (D$_2$O with TMS capillary):δ2.54 (s, 3H), 3.94 (t, 2H), 4.93 (t, 2H).

EXAMPLE 5

Preparation of 2,2-Dinitrobutane-1,4-diol-4-acetate

To a stirred solution of 18.2 g (0.079 mole) of crude potassium 3,3-dinitropropyl acetate in 200 ml of distilled water at ambient temperature was added 19 ml of 36% formalin. Concentrated hydrochloric acid (7.3 ml) was added in portions over 10 minutes. At this point there is appreciable oil precipitate and the aqueous phase is only slightly yellow in color (pH about 4). After the reaction mixture was stirred for 2 hours at ambient temperature the oil was extracted into methylene chloride to give 17.3 g (89%) of product which was crystallized by cooling a chloroform-hexane solution in dry ice-acetone yielding 13.63 g (78%) of white crystals, mp 20°–21.5° C.: $^1$H-NMR (CD$_2$Cl$_2$): δ4.58 (d, 2H), 4.33 (t, 2H), 3.51 (t, 1H), 3.06 (t, 2H), 2.06 (s, 3H).

Analysis

Calculated for C$_6$H$_{10}$N$_2$O$_7$: C, 32.44; H, 4.54; N, 12.61. Found: C, 32.40; H, 4.56; N, 12.59.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. An ester of the formula

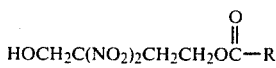

wherein R is selected from the group consisting of alkyl groups, fluoroalkyl groups, chloroalkyl groups, aryl groups, fluoroaryl groups, chloroaryl groups, aralkyl groups, fluoroaralkyl groups, chloroaralkyl groups, and alkene groups.

2. The ester of claim 1 wherein R is selected from the group consisting of alkyl groups, fluoroalkyl groups, and chloroalkyl groups.

3. The ester of claim 2 of wherein R contains from 1 to 12 carbon atoms.

4. The ester of claim 3 wherein R contains from 1 to 4 carbon atoms.

5. The ester of claim 1 wherein R is selected from the group consisting of aryl groups, fluoroaryl groups, and chloroaryl groups.

6. The ester of claim 5 wherein R contains from 6 to 18 carbon atoms.

7. The ester of claim 6 wherein R contains 6 carbon atoms.

8. The ester of claim 1 wherein R is selected from the group consisting of aralkyl groups, fluoroaralkyl groups, and chloroaralkyl groups.

9. The ester of claim 8 wherein R contains from 7 to 18 carbon atoms.

10. The ester of claim 9 wherein R contains from 7 to 10 carbon atoms.

11. The ester of claim 1 wherein R is vinyl.

* * * * *